(12) United States Patent
Govari et al.

(10) Patent No.: US 11,974,803 B2
(45) Date of Patent: May 7, 2024

(54) BASKET CATHETER WITH BALLOON

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Andres Claudio Altmann, Haifa (IL); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 242 days.

(21) Appl. No.: 17/068,395

(22) Filed: Oct. 12, 2020

(65) Prior Publication Data

US 2022/0110675 A1    Apr. 14, 2022

(51) Int. Cl.
*A61B 18/14*    (2006.01)
*A61B 17/00*    (2006.01)
(Continued)

(52) U.S. Cl.
CPC ...... *A61B 18/1492* (2013.01); *A61B 18/1206* (2013.01); *A61B 2017/00867* (2013.01);
(Continued)

(58) Field of Classification Search
CPC .. A61B 2018/00267; A61B 2018/1472; A61B 2018/0022; A61B 2018/00255; A61B 2018/00029; A61B 2018/00613; A61B 2018/00577; A61B 2018/00214; A61B 2018/00011; A61B 2018/00005; A61B 2017/00867; A61B 2017/22051;
(Continued)

(56) References Cited

U.S. PATENT DOCUMENTS

D123,782 S    12/1940 Paul
3,316,896 A    5/1967 Louis
(Continued)

FOREIGN PATENT DOCUMENTS

CN    101422637 A    5/2009
CN    102271607 A    12/2011
(Continued)

OTHER PUBLICATIONS

Partial European Search Report dated Mar. 14, 2022, from corresponding European Application No. 21201890.7.
(Continued)

*Primary Examiner* — Khadijeh A Vahdat
*Assistant Examiner* — Marina Delaney Templeton
(74) *Attorney, Agent, or Firm* — Troutman Pepper Hamilton Sanders LLP

(57) ABSTRACT

In one embodiment, a catheter apparatus is configured to be inserted into a body part of a living subject, and including an elongated deflectable element including a distal end, an expandable basket assembly disposed at the distal end and comprising a plurality of splines and a plurality of electrodes disposed on the splines, an irrigation channel disposed in the elongated deflectable element, and an inflatable balloon disposed in the expandable basket assembly and including a plurality of irrigation holes in fluid connection with the irrigation channel.

14 Claims, 7 Drawing Sheets

(51) Int. Cl.
*A61B 18/00* (2006.01)
*A61B 18/12* (2006.01)

(52) U.S. Cl.
CPC .............. *A61B 2018/00029* (2013.01); *A61B 2018/0022* (2013.01); *A61B 2018/00267* (2013.01); *A61B 2018/00357* (2013.01); *A61B 2018/00577* (2013.01); *A61B 2218/002* (2013.01)

(58) Field of Classification Search
CPC .... A61B 2017/320084; A61B 18/1492; A61B 2217/007; A61B 2218/002
See application file for complete search history.

(56) References Cited

U.S. PATENT DOCUMENTS

| | | |
|---|---|---|
| 4,276,874 A | 7/1981 | Wolvek et al. |
| 4,587,975 A | 5/1986 | Salo et al. |
| 4,699,147 A | 10/1987 | Chilson et al. |
| 4,709,698 A | 12/1987 | Johnston et al. |
| 4,805,621 A | 2/1989 | Heinze et al. |
| 4,940,064 A | 7/1990 | Desai |
| 5,178,957 A | 1/1993 | Kolpe et al. |
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,391,199 A | 2/1995 | Ben |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,429,617 A | 7/1995 | Hammersmark et al. |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,582,609 A | 12/1996 | Swanson et al. |
| 5,584,830 A | 12/1996 | Ladd et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,702,386 A | 12/1997 | Stern et al. |
| 5,718,241 A | 2/1998 | Ben-Haim et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,797,903 A | 8/1998 | Swanson et al. |
| 5,823,189 A | 10/1998 | Kordis |
| 5,860,974 A | 1/1999 | Abele |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 5,971,983 A | 10/1999 | Lesh |
| 6,012,457 A | 1/2000 | Lesh |
| 6,014,579 A | 1/2000 | Pomeranz et al. |
| 6,014,590 A | 1/2000 | Whayne et al. |
| 6,024,740 A | 2/2000 | Lesh et al. |
| 6,042,580 A | 3/2000 | Simpson |
| 6,119,030 A | 9/2000 | Morency |
| 6,123,718 A | 9/2000 | Tu et al. |
| 6,142,993 A * | 11/2000 | Whayne .............. A61B 18/1492 606/41 |
| 6,164,283 A | 12/2000 | Lesh |
| 6,171,275 B1 | 1/2001 | Webster, Jr. |
| 6,176,832 B1 | 1/2001 | Habu et al. |
| 6,198,974 B1 | 3/2001 | Webster, Jr. |
| 6,216,043 B1 | 4/2001 | Swanson et al. |
| 6,216,044 B1 | 4/2001 | Kordis |
| 6,226,542 B1 | 5/2001 | Reisfeld |
| 6,239,724 B1 | 5/2001 | Doron |
| 6,301,496 B1 | 10/2001 | Reisfeld |
| 6,322,558 B1 | 11/2001 | Taylor et al. |
| 6,332,089 B1 | 12/2001 | Acker |
| 6,380,957 B1 | 4/2002 | Banning |
| 6,402,740 B1 | 6/2002 | Ellis et al. |
| 6,428,537 B1 | 8/2002 | Swanson et al. |
| D462,389 S | 9/2002 | Provence et al. |
| 6,456,864 B1 | 9/2002 | Swanson et al. |
| 6,471,693 B1 | 10/2002 | Carroll et al. |
| 6,484,118 B1 | 11/2002 | Govari |
| 6,522,930 B1 | 2/2003 | Schaer et al. |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker |
| 6,656,174 B1 | 12/2003 | Hegde et al. |
| 6,690,963 B2 | 2/2004 | Ben |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,814,733 B2 | 11/2004 | Schwartz et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,893,433 B2 | 5/2005 | Lentz |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 6,986,744 B1 | 1/2006 | Krivitski |
| 6,987,995 B2 | 1/2006 | Drysen |
| 6,997,924 B2 | 2/2006 | Schwartz et al. |
| 7,048,734 B1 | 5/2006 | Fleischman et al. |
| 7,142,903 B2 | 11/2006 | Rodriguez et al. |
| 7,149,563 B2 | 12/2006 | Fuimaono et al. |
| 7,156,816 B2 | 1/2007 | Schwartz et al. |
| 7,255,695 B2 | 8/2007 | Falwell et al. |
| 7,257,434 B2 | 8/2007 | Fuimaono et al. |
| 7,274,957 B2 | 9/2007 | Drysen |
| 7,340,307 B2 | 3/2008 | Maguire et al. |
| 7,377,906 B2 | 5/2008 | Selkee |
| 7,399,299 B2 | 7/2008 | Daniel et al. |
| 7,410,486 B2 | 8/2008 | Fuimaono et al. |
| 7,442,190 B2 | 10/2008 | Abbound et al. |
| 7,522,950 B2 | 4/2009 | Fuimaono et al. |
| 7,536,218 B2 | 5/2009 | Govari et al. |
| 7,591,799 B2 | 9/2009 | Selkee |
| 7,593,760 B2 | 9/2009 | Rodriguez et al. |
| RE41,334 E | 5/2010 | Beatty et al. |
| 7,720,517 B2 | 5/2010 | Drysen |
| 7,756,576 B2 | 7/2010 | Levin |
| 7,842,031 B2 | 11/2010 | Abboud et al. |
| 7,846,157 B2 | 12/2010 | Kozel |
| 7,853,302 B2 | 12/2010 | Rodriguez et al. |
| 7,930,018 B2 | 4/2011 | Harlev et al. |
| 8,000,765 B2 | 8/2011 | Rodriguez et al. |
| 8,007,495 B2 | 8/2011 | McDaniel et al. |
| 8,021,327 B2 | 9/2011 | Selkee |
| 8,048,032 B2 | 11/2011 | Root et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,231,617 B2 | 7/2012 | Satake |
| 8,235,988 B2 | 8/2012 | Davis et al. |

(56) References Cited

U.S. PATENT DOCUMENTS

| | | |
|---|---|---|
| 8,267,932 B2 | 9/2012 | Baxter et al. |
| 8,275,440 B2 | 9/2012 | Rodriguez et al. |
| 8,346,339 B2 | 1/2013 | Kordis et al. |
| 8,348,888 B2 | 1/2013 | Selkee |
| 8,357,152 B2 | 1/2013 | Govari et al. |
| D682,289 S | 5/2013 | DiJulio et al. |
| D682,291 S | 5/2013 | Baek et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| D690,318 S | 9/2013 | Kluttz et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| D694,652 S | 12/2013 | Tompkin |
| 8,641,709 B2 | 2/2014 | Sauvageau et al. |
| 8,712,550 B2 | 4/2014 | Grunewald |
| 8,721,590 B2 | 5/2014 | Seward et al. |
| 8,755,861 B2 | 6/2014 | Harlev et al. |
| 8,777,161 B2 | 7/2014 | Pollock et al. |
| 8,825,130 B2 | 9/2014 | Just et al. |
| D716,340 S | 10/2014 | Bresin et al. |
| 8,852,181 B2 | 10/2014 | Malecki et al. |
| 8,906,011 B2 | 12/2014 | Gelbart et al. |
| D720,766 S | 1/2015 | Mandal et al. |
| D721,379 S | 1/2015 | Moon et al. |
| 8,945,120 B2 | 2/2015 | McDaniel et al. |
| D724,618 S | 3/2015 | Shin |
| 8,979,839 B2 | 3/2015 | De La Rama et al. |
| 8,998,893 B2 | 4/2015 | Avitall |
| D729,263 S | 5/2015 | Ahn et al. |
| 9,037,264 B2 | 5/2015 | Just et al. |
| 9,060,756 B2 | 6/2015 | Bencini |
| 9,089,350 B2 | 7/2015 | Willard |
| D736,780 S | 8/2015 | Wang |
| 9,126,023 B1 | 9/2015 | Sahatjian et al. |
| 9,131,980 B2 | 9/2015 | Bloom |
| D740,308 S | 10/2015 | Kim et al. |
| D743,424 S | 11/2015 | Danielyan et al. |
| D744,000 S | 11/2015 | Villamor et al. |
| 9,173,758 B2 | 11/2015 | Brister et al. |
| 9,204,929 B2 | 12/2015 | Solis |
| D747,742 S | 1/2016 | Fan et al. |
| D750,644 S | 3/2016 | Bhutani et al. |
| 9,277,960 B2 | 3/2016 | Weinkam et al. |
| 9,283,034 B2 | 3/2016 | Katoh et al. |
| 9,289,141 B2 | 3/2016 | Lowery et al. |
| D753,690 S | 4/2016 | Vazquez et al. |
| 9,314,208 B1 | 4/2016 | Altmann et al. |
| 9,320,631 B2 | 4/2016 | Moore et al. |
| 9,339,331 B2 | 5/2016 | Tegg et al. |
| 9,345,540 B2 | 5/2016 | Mallin et al. |
| D759,673 S | 6/2016 | Looney et al. |
| D759,675 S | 6/2016 | Looney et al. |
| D764,500 S | 8/2016 | Wang |
| D765,709 S | 9/2016 | Gagnier |
| D767,616 S | 9/2016 | Jones et al. |
| D768,696 S | 10/2016 | Gagnier |
| 9,474,486 B2 | 10/2016 | Eliason |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| D783,037 S | 4/2017 | Hariharan et al. |
| 9,655,677 B2 | 5/2017 | Salahieh et al. |
| 9,687,297 B2 | 6/2017 | Just et al. |
| D791,805 S | 7/2017 | Segars |
| 9,693,733 B2 | 7/2017 | Altmann et al. |
| 9,757,180 B2 | 9/2017 | Gelfand |
| 9,782,099 B2 | 10/2017 | Williams et al. |
| 9,788,895 B2 | 10/2017 | Solis |
| 9,795,442 B2 | 10/2017 | Salahieh et al. |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,907,610 B2 | 3/2018 | Beeckler et al. |
| 9,956,035 B2 | 5/2018 | Govari et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,952 B2 | 7/2019 | Basu |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| D861,717 S | 10/2019 | Brekke et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,688,278 B2 | 6/2020 | Beeckler et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |

(56) References Cited

U.S. PATENT DOCUMENTS

| | | |
|---|---|---|
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2001/0031961 A1 | 10/2001 | Hooven |
| 2002/0002369 A1 | 1/2002 | Hood |
| 2002/0006455 A1 | 1/2002 | Levine |
| 2002/0065455 A1 | 5/2002 | Ben-Haim et al. |
| 2002/0068931 A1 | 6/2002 | Wong et al. |
| 2002/0077627 A1 | 6/2002 | Johnson et al. |
| 2002/0160134 A1 | 10/2002 | Ogushi et al. |
| 2003/0018327 A1 | 1/2003 | Truckai et al. |
| 2003/0028183 A1 | 2/2003 | Sanchez et al. |
| 2003/0050637 A1 | 3/2003 | Maguire et al. |
| 2003/0060820 A1 | 3/2003 | Maguire et al. |
| 2003/0120150 A1 | 6/2003 | Govari |
| 2003/0144658 A1 | 7/2003 | Schwartz et al. |
| 2004/0068178 A1 | 4/2004 | Govari |
| 2004/0122445 A1 | 6/2004 | Butler et al. |
| 2004/0147920 A1 | 7/2004 | Keidar |
| 2004/0210121 A1 | 10/2004 | Fuimaono et al. |
| 2004/0225285 A1 | 11/2004 | Gibson |
| 2005/0070887 A1 | 3/2005 | Taimisto et al. |
| 2005/0096647 A1 | 5/2005 | Steinke et al. |
| 2005/0119686 A1 | 6/2005 | Clubb |
| 2006/0009689 A1 | 1/2006 | Fuimaono et al. |
| 2006/0009690 A1 | 1/2006 | Fuimaono et al. |
| 2006/0013595 A1 | 1/2006 | Trezza et al. |
| 2006/0100669 A1 | 5/2006 | Fuimaono et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0093806 A1 | 4/2007 | Desai et al. |
| 2007/0276212 A1 | 11/2007 | Fuimaono et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0051707 A1 | 2/2008 | Phan et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0234564 A1 | 9/2008 | Beatty et al. |
| 2008/0249463 A1 | 10/2008 | Pappone et al. |
| 2008/0262489 A1 | 10/2008 | Steinke |
| 2008/0281312 A1 | 11/2008 | Werneth et al. |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0118726 A1 | 5/2011 | De La Rama et al. |
| 2011/0130648 A1 | 6/2011 | Beeckler et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0301597 A1 | 12/2011 | McDaniel et al. |
| 2011/0313286 A1 | 12/2011 | Whayne et al. |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0136350 A1* | 5/2012 | Goshgarian ........ A61B 18/1492 606/41 |
| 2012/0143177 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0085493 A1* | 4/2013 | Bloom ............... A61B 18/1492 606/41 |
| 2013/0090649 A1 | 4/2013 | Smith et al. |
| 2013/0090651 A1* | 4/2013 | Smith ................ A61B 18/1492 606/41 |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0197499 A1 | 8/2013 | Lalonde et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0296852 A1 | 11/2013 | Madjarov et al. |
| 2013/0318439 A1 | 11/2013 | Landis et al. |
| 2014/0012242 A1 | 1/2014 | Lee et al. |
| 2014/0018788 A1 | 1/2014 | Engelman et al. |
| 2014/0025069 A1 | 1/2014 | Willard et al. |
| 2014/0031813 A1 | 1/2014 | Tellio et al. |
| 2014/0052118 A1 | 2/2014 | Laske et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0227437 A1 | 8/2014 | DeBoer et al. |
| 2014/0243821 A1 | 8/2014 | Salahieh et al. |
| 2014/0257069 A1 | 9/2014 | Eliason et al. |
| 2014/0275993 A1 | 9/2014 | Ballakur |
| 2014/0276712 A1 | 9/2014 | Mallin et al. |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0309512 A1 | 10/2014 | Govari et al. |
| 2014/0330266 A1 | 11/2014 | Thompson et al. |
| 2014/0357956 A1 | 12/2014 | Salahieh et al. |
| 2015/0005799 A1 | 1/2015 | Lindquist et al. |
| 2015/0011991 A1 | 1/2015 | Buysman et al. |
| 2015/0025532 A1 | 1/2015 | Hanson et al. |
| 2015/0025533 A1 | 1/2015 | Groff et al. |
| 2015/0045863 A1 | 2/2015 | Litscher et al. |
| 2015/0057655 A1 | 2/2015 | Osypka |
| 2015/0067512 A1 | 3/2015 | Roswell |
| 2015/0080693 A1 | 3/2015 | Solis |
| 2015/0080883 A1 | 3/2015 | Haverkost et al. |
| 2015/0105770 A1 | 4/2015 | Amit |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0119878 A1 | 4/2015 | Heisel et al. |
| 2015/0133919 A1 | 5/2015 | McDaniel et al. |
| 2015/0141982 A1 | 5/2015 | Lee |
| 2015/0157382 A1 | 6/2015 | Avitall et al. |
| 2015/0196740 A1 | 7/2015 | Mallin et al. |

(56) References Cited

U.S. PATENT DOCUMENTS

| | | |
|---|---|---|
| 2015/0208942 A1 | 7/2015 | Bar-Tal et al. |
| 2015/0216591 A1 | 8/2015 | Cao et al. |
| 2015/0216650 A1 | 8/2015 | Shaltis |
| 2015/0250424 A1 | 9/2015 | Govari et al. |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0270634 A1 | 9/2015 | Buesseler et al. |
| 2015/0272667 A1 | 10/2015 | Govari et al. |
| 2015/0327805 A1 | 11/2015 | Ben-Haim |
| 2015/0341752 A1 | 11/2015 | Flynn |
| 2015/0342532 A1 | 12/2015 | Basu et al. |
| 2016/0000499 A1 | 1/2016 | Lennox et al. |
| 2016/0051321 A1 | 2/2016 | Salahieh et al. |
| 2016/0081746 A1 | 3/2016 | Solis |
| 2016/0085431 A1 | 3/2016 | Kim et al. |
| 2016/0106499 A1 | 4/2016 | Ogata et al. |
| 2016/0113582 A1 | 4/2016 | Altmann et al. |
| 2016/0113709 A1 | 4/2016 | Maor |
| 2016/0166306 A1 | 6/2016 | Pageard |
| 2016/0175041 A1 | 6/2016 | Govari et al. |
| 2016/0183877 A1 | 6/2016 | Williams et al. |
| 2016/0196635 A1 | 7/2016 | Cho et al. |
| 2016/0228023 A1 | 8/2016 | Govari |
| 2016/0228062 A1 | 8/2016 | Altmann et al. |
| 2016/0256305 A1 | 9/2016 | Longo et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2016/0374748 A9 | 12/2016 | Salahieh et al. |
| 2017/0027638 A1 | 2/2017 | Solis |
| 2017/0042614 A1 | 2/2017 | Salahieh et al. |
| 2017/0042615 A1 | 2/2017 | Salahieh et al. |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0080192 A1 | 3/2017 | Giasolli et al. |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0143359 A1 | 5/2017 | Nguyen et al. |
| 2017/0156790 A1 | 6/2017 | Aujla |
| 2017/0164464 A1 | 6/2017 | Weinkam et al. |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0311829 A1 | 11/2017 | Beeckler et al. |
| 2017/0311893 A1 | 11/2017 | Beeckler et al. |
| 2017/0312012 A1* | 11/2017 | Harlev ............... A61M 25/001 |
| 2017/0312022 A1 | 11/2017 | Beeckler et al. |
| 2017/0312420 A1* | 11/2017 | Harlev ............... A61M 25/001 |
| 2017/0347896 A1 | 12/2017 | Keyes et al. |
| 2017/0347959 A1 | 12/2017 | Guta et al. |
| 2017/0348049 A1* | 12/2017 | Vrba ............... A61B 18/1492 |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0028084 A1 | 2/2018 | Williams et al. |
| 2018/0049803 A1 | 2/2018 | Solis |
| 2018/0074693 A1 | 3/2018 | Jones et al. |
| 2018/0082203 A1 | 3/2018 | Bender et al. |
| 2018/0085064 A1 | 3/2018 | Auerbach et al. |
| 2018/0110562 A1 | 4/2018 | Govari et al. |
| 2018/0125575 A1 | 5/2018 | Schwartz et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0161093 A1* | 6/2018 | Basu ............... A61M 25/1018 |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0256247 A1 | 9/2018 | Govari et al. |
| 2018/0279954 A1 | 10/2018 | Hayam et al. |
| 2018/0280080 A1 | 10/2018 | Govari et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0333162 A1 | 11/2018 | Saab |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2018/0368927 A1 | 12/2018 | Lyons et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0059818 A1 | 2/2019 | Herrera et al. |
| 2019/0060622 A1 | 2/2019 | Beeckler |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117301 A1 | 4/2019 | Steinke |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0143079 A1 | 5/2019 | Beeckler et al. |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0175262 A1 | 6/2019 | Govari et al. |
| 2019/0175263 A1 | 6/2019 | Altmann et al. |
| 2019/0183567 A1 | 6/2019 | Govari et al. |
| 2019/0188909 A1 | 6/2019 | Yellin et al. |
| 2019/0201664 A1 | 7/2019 | Govari |
| 2019/0201669 A1 | 7/2019 | Govari et al. |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0217065 A1 | 7/2019 | Govari et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246395 A1 | 8/2019 | Govari et al. |
| 2019/0297441 A1 | 9/2019 | Dehe et al. |
| 2019/0298441 A1 | 10/2019 | Clark et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2019/0365451 A1 | 12/2019 | Jung, Jr. |
| 2020/0000518 A1 | 1/2020 | Kiernan et al. |
| 2020/0001054 A1 | 1/2020 | Jimenez et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015693 A1 | 1/2020 | Beeckler et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |

(56) References Cited

U.S. PATENT DOCUMENTS

| | | | |
|---|---|---|---|
| 2020/0085497 A1 | 3/2020 | Zhang et al. | |
| 2020/0093539 A1 | 3/2020 | Long et al. | |
| 2020/0129089 A1 | 4/2020 | Gliner et al. | |
| 2020/0129125 A1 | 4/2020 | Govari et al. | |
| 2020/0129128 A1 | 4/2020 | Gliner et al. | |
| 2020/0155226 A1 | 5/2020 | Valls et al. | |
| 2020/0163707 A1* | 5/2020 | Sliwa | A61B 18/082 |
| 2020/0179650 A1 | 6/2020 | Beeckler et al. | |
| 2020/0196896 A1 | 6/2020 | Solis | |
| 2020/0205689 A1 | 7/2020 | Squires et al. | |
| 2020/0205690 A1 | 7/2020 | Williams et al. | |
| 2020/0205737 A1 | 7/2020 | Beeckler | |
| 2020/0205876 A1 | 7/2020 | Govari | |
| 2020/0205892 A1 | 7/2020 | Viswanathan et al. | |
| 2020/0206461 A1 | 7/2020 | Govari et al. | |
| 2020/0206498 A1 | 7/2020 | Arora et al. | |
| 2020/0289197 A1 | 9/2020 | Viswanathan et al. | |
| 2020/0297234 A1 | 9/2020 | Houben et al. | |
| 2020/0297281 A1 | 9/2020 | Basu et al. | |
| 2020/0305726 A1 | 10/2020 | Salvestro et al. | |
| 2020/0305946 A1 | 10/2020 | DeSimone et al. | |
| 2020/0397328 A1 | 12/2020 | Altmann et al. | |
| 2020/0398048 A1 | 12/2020 | Krimsky et al. | |
| 2021/0015549 A1 | 1/2021 | Haghighi-Mood et al. | |
| 2021/0022684 A1 | 1/2021 | Govari et al. | |
| 2021/0045805 A1 | 2/2021 | Govari et al. | |
| 2021/0059549 A1 | 3/2021 | Urman et al. | |
| 2021/0059550 A1 | 3/2021 | Urman et al. | |
| 2021/0059608 A1 | 3/2021 | Beeckler et al. | |
| 2021/0059743 A1 | 3/2021 | Govari | |
| 2021/0059747 A1 | 3/2021 | Krans et al. | |
| 2021/0077184 A1 | 3/2021 | Basu et al. | |
| 2021/0082157 A1 | 3/2021 | Rosenberg et al. | |
| 2021/0085200 A1 | 3/2021 | Auerbach et al. | |
| 2021/0085204 A1 | 3/2021 | Auerbach et al. | |
| 2021/0085215 A1 | 3/2021 | Auerbach et al. | |
| 2021/0085387 A1 | 3/2021 | Amit et al. | |
| 2021/0093292 A1 | 4/2021 | Baram et al. | |
| 2021/0093294 A1 | 4/2021 | Shemesh et al. | |
| 2021/0093374 A1 | 4/2021 | Govari et al. | |
| 2021/0093377 A1 | 4/2021 | Herrera et al. | |
| 2021/0100612 A1 | 4/2021 | Baron et al. | |
| 2021/0113822 A1 | 4/2021 | Beeckler et al. | |
| 2021/0127999 A1 | 5/2021 | Govari et al. | |
| 2021/0128010 A1 | 5/2021 | Govari et al. | |
| 2021/0133516 A1 | 5/2021 | Govari et al. | |
| 2021/0145282 A1 | 5/2021 | Bar-Tal et al. | |
| 2021/0169421 A1 | 6/2021 | Govari | |
| 2021/0169567 A1 | 6/2021 | Govari et al. | |
| 2021/0169568 A1 | 6/2021 | Govari et al. | |
| 2021/0177294 A1 | 6/2021 | Gliner et al. | |
| 2021/0177356 A1 | 6/2021 | Gliner et al. | |
| 2021/0178166 A1 | 6/2021 | Govari et al. | |
| 2021/0186363 A1 | 6/2021 | Gliner et al. | |
| 2021/0187241 A1 | 6/2021 | Govari et al. | |
| 2021/0196372 A1 | 7/2021 | Altmann et al. | |
| 2021/0196394 A1 | 7/2021 | Govari et al. | |
| 2021/0212591 A1 | 7/2021 | Govari et al. | |
| 2021/0219904 A1 | 7/2021 | Yarnitsky et al. | |
| 2021/0278936 A1 | 9/2021 | Katz et al. | |
| 2021/0282659 A1 | 9/2021 | Govari et al. | |
| 2021/0307815 A1 | 10/2021 | Govari et al. | |
| 2021/0308424 A1 | 10/2021 | Beeckler et al. | |
| 2021/0338319 A1 | 11/2021 | Govari et al. | |

FOREIGN PATENT DOCUMENTS

| | | |
|---|---|---|
| CN | 102458566 A | 5/2012 |
| CN | 203539434 U | 4/2014 |
| CN | 104244856 A | 12/2014 |
| CN | 14546117 A | 4/2015 |
| CN | 105150844 A | 12/2015 |
| CN | 105473091 A | 4/2016 |
| CN | 105473093 A | 4/2016 |
| CN | 11248996 A | 6/2020 |
| CN | 111248993 A | 6/2020 |
| EP | 0668740 A1 | 8/1995 |
| EP | 0779059 A1 | 6/1997 |
| EP | 0644738 B1 | 3/2000 |
| EP | 0727183 B1 | 11/2002 |
| EP | 0727184 B1 | 12/2002 |
| EP | 1790304 A2 | 5/2007 |
| EP | 2749214 A1 | 7/2014 |
| EP | 2783651 A1 | 10/2014 |
| EP | 2865350 A2 | 4/2015 |
| EP | 2875790 A2 | 5/2015 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 3238646 A2 | 11/2017 |
| EP | 3238648 A1 | 11/2017 |
| EP | 32516622 A1 | 12/2017 |
| EP | 2887931 B1 | 1/2018 |
| EP | 3300680 A1 | 4/2018 |
| EP | 3315087 A1 | 5/2018 |
| EP | 3332727 A2 | 6/2018 |
| EP | 2349440 B1 | 8/2019 |
| EP | 3571983 A2 | 11/2019 |
| EP | 3318211 B1 | 12/2019 |
| EP | 3581135 A1 | 12/2019 |
| EP | 3586778 A1 | 1/2020 |
| EP | 2736434 B1 | 2/2020 |
| EP | 3451962 B1 | 3/2020 |
| EP | 3653153 A1 | 5/2020 |
| EP | 3972510 A1 | 3/2022 |
| JP | H6261951 A | 9/1994 |
| JP | H1176223 A | 3/1999 |
| JP | 2000504242 A | 4/2000 |
| JP | 2005052424 A | 3/2005 |
| JP | 2010507404 A | 3/2010 |
| JP | 2012024156 A | 2/2012 |
| JP | 2013013726 A | 1/2013 |
| JP | 2013078587 A | 5/2013 |
| JP | 2013529109 A | 7/2013 |
| JP | 20145229419 A | 11/2014 |
| JP | 2015503365 A | 2/2015 |
| JP | 2015100706 A | 6/2015 |
| JP | 2015112113 A | 6/2015 |
| JP | 2015112114 A | 6/2015 |
| JP | 2015518776 A | 7/2015 |
| JP | 2016515442 A | 5/2016 |
| JP | 2016116863 A | 6/2016 |
| WO | 9421167 A1 | 9/1994 |
| WO | 9421169 A1 | 9/1994 |
| WO | WO1996005768 A1 | 2/1996 |
| WO | 9625095 A1 | 8/1996 |
| WO | 9634560 A1 | 11/1996 |
| WO | 0056237 A2 | 9/2000 |
| WO | 0182814 B1 | 5/2002 |
| WO | 021102231 A2 | 12/2002 |
| WO | 2004087249 A2 | 10/2004 |
| WO | 2005041748 A2 | 5/2005 |
| WO | 2008049087 A2 | 4/2008 |
| WO | 2011143468 A2 | 11/2011 |
| WO | 2012100185 A2 | 7/2012 |
| WO | 2013049601 A2 | 4/2013 |
| WO | 2013052852 A1 | 4/2013 |
| WO | 2013052919 A2 | 4/2013 |
| WO | 2013154776 A2 | 10/2013 |
| WO | 2013162884 A1 | 10/2013 |
| WO | 2013173917 A1 | 11/2013 |
| WO | 2013176881 A1 | 11/2013 |
| WO | 2014168987 A1 | 10/2014 |
| WO | 2017176205 A1 | 10/2014 |
| WO | 2015049784 A1 | 4/2015 |
| WO | 2015/200518 A1 | 12/2015 |
| WO | 2016019760 A1 | 2/2016 |
| WO | 2016044687 A1 | 3/2016 |
| WO | 2016183337 A2 | 11/2016 |
| WO | 2016210437 A1 | 12/2016 |
| WO | 2017024306 A1 | 2/2017 |

(56) References Cited

FOREIGN PATENT DOCUMENTS

| WO | 2017087549 A1 | 5/2017 |
|---|---|---|
| WO | 2018106569 A1 | 6/2018 |
| WO | 2018111600 A1 | 6/2018 |
| WO | 2018129133 A1 | 7/2018 |
| WO | 2018191149 A1 | 10/2018 |
| WO | 2019084442 A1 | 5/2019 |
| WO | 2019095020 A1 | 5/2019 |
| WO | 2019143960 A1 | 7/2019 |
| WO | 2020062617 A1 | 2/2020 |
| WO | 2020026328 A1 | 10/2020 |
| WO | 2021/119479 A1 | 6/2021 |

OTHER PUBLICATIONS

Extended European Search Report dated Jun. 14, 2022, from corresponding European Application No. 21201890.7.
Angelo O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages [Retrieved on Dec. 16, 2020] Retrieved from URL: https://cardiacrhythmnews/first-in-man-study-shows-promising-results-with-a-multi-electrode-radiofrequency-balloon-for-paroxysmal-af-treatment/.
Casella M., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.
Co-Pending U.S. Appl. No. 14/578,807, filed Dec. 22, 2014, 21 pages.
Das, M., et al., "Ablational Index, a Novel Narker of Ablation Lesion Quality: Prediction of Pulmonary Vein Reconnection at Repeat Electrophysiology, Study and Regional Differences in Target Values," Eurospace, 2017, Publsihed Online May 31, 2016, vol. 19, pp. 775-783.
Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.
Extended European Search Report for European Application No. EP17168513.4 mailed Sep. 18, 2017, 11 pages.
Extended European Search Report for European Application No. 15201723.2, mailed May 11, 2016, 07 Pages.
Extended European Search Report for European Application No. 17168393.1 mailed Dec. 15, 2017, 12 Pages.
Extended European Search Report for European Application No. 17168518.3, mailed Sep. 20, 2017, 9 Pages.
Extended European Search Report for European Application No. 17173893.3, mailed Nov. 6, 2017, 8 Pages.
Extended European Search Report for European Application No. 17201434.2, mailed Feb. 1, 2018, 10 Pages.
Extended European Search Report for European Application No. 17205876.0, mailed Jun. 1, 2018, 13 Pages.
Extended European Search Report for European Application No. 19177365.4, mailed Nov. 8, 2019, 7 Pages.
Extended European Search Report for European Application No. 19183327.6, mailed Nov. 21, 2019, 8 Pages.
Extended European Search Report for European Application No. 20153872.5, mailed May 7, 2020, 9 Pages.
Extended European Search Report for European Application No. 20195648.9, mailed Feb. 12, 2021, 8 Pages.
Fornell D., "Multi-Electrode RF Balloon Efficient for Acute Pulmonary Vein Isolation," Diagnostic and Interventinal Cardiology, May 17, 2017, 3 Pages, [Retrieved on Dec. 16, 2020]Retrieved from URL: www.dicardiology.com/article/multi-electrode-rf-balloon-efficient-for-acute-pulmonary-vein-isolation.
Haines D.E., et al., "The Promise of Pulsed Field Ablation," Dec. 2019, vol. 19, No. 12, 10 pages.
Honarbakhsh S., et al., "Radiofrequency Balloon Catheter Ablation for Paroxysmal Artial Fibrillation, Radiance Study—a UK experience," EP Europace, Oct. 2017, vol. 19, No. 1, p. i21, 3 Pages.
International Search Report and Written Opinion for International Application No. PCT/IB2019/052313, mailed Jul. 22, 2019, 8 Pages.
International Search Report and Written Opinion for International Application No. PCT/IB2019/056381, mailed Dec. 17, 2019, 10 pages.
International Search Report and Written Opinion for International Application No. PCT/IB2019/057743, mailed Dec. 6, 2019, 16 Pages.
International Search Report and Written Opinion issued in corresponding International Application No. PCT/IB2019/057742, dated Nov. 28, 2019, 18 Pages.
Nagashima K., et al., "Hot Balloon Versus Cryoballoon Ablation for Atrial Fibrillation," Circulation: Arrythmia and Electrophysiology, May 2018, vol. 11, No. 5, e005861, 9 Pages.
Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://acc.org/about-acc/press-releases/2017/03/18/08/47/sun-1045am-for-atrial-fibrillation-ablation-newer-anticoagulant-reduces-major-bleeds.
Okano T., "Wire Perforation Casuing Cardiopulomary Arrest During Radiofrequency Hot Balloon Ablation for Pulmonary Vein Isolation," Journal of Cardiology Cases, Feb. 15, 2019, vol. 19, No. 5, pp. 169-172.
Partial European Search Report for European Application No. 17168393.1 mailed Sep. 13, 2017, 13 Pages.
Partial European Search Report for European Application No. 17205876.0, mailed Feb. 22, 2018, 10 Pages.
Reddy V.Y., et al., "Balloon Catheter Ablation to Treat Paroxysmal Atrial Fibrillation: What is the Level of Pulomary Venous Isolation?," Heart Rythym, Mar. 2008, vol. 5, No. 3, pp. 353-360, 3 Pages.
Winkle R.A., et al., "Atrial Fibrillation Ablation Using Open-Irrigated Tip Radiofrequency: Experience with Intraprocedural Activated Clotting Times ≤120 Seconds," Heart Rythym, Jun. 2014, Epub Mar. 27, 2014, vol. 11, No. 6, pp. 963-968.
YouTube: "Intensity™ CX4 Professional E-Stim/ Ultrasound Combo," Dec. 22, 2015, 1 Page, [Retrieived on Nov. 19, 2020], Retrieved from URL: https://www.youtube.com/watch?v=76s1QkMWJME].
YouTube: "New Interface TactoCath Contact Force Ablation Catheter," Nov. 26, 2013, 1 Pages, [Retrieived on Nov. 19, 2020], Retrieved from URL: https: /Avww.youtube.com/watch?v=aYvYO8Hpylg].

\* cited by examiner

BASKET CATHETER WITH BALLOON

FIELD OF THE INVENTION

The present invention relates to medical devices, and in particular, but not exclusively to, catheters.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/006455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally adhered to the skin of the patient or by means of a second catheter that is positioned in or near the heart. RF (radio frequency) current is applied between the catheter electrode(s) of the ablating catheter and an indifferent electrode (which may be one of the catheter electrodes), and current flows through the media between the electrodes, i.e., blood and tissue. The distribution of current may depend on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. In some applications, irreversible electroporation may be performed to ablate the tissue.

US Patent Publication 2019/0117301 of Steinke, et al., describes a catheter and catheter system for treatment of a blood vessel of a patient including an elongate flexible catheter body with a radially expandable structure. A plurality of electrodes or other electrosurgical energy delivery surfaces can radially engage material to be treated when the structure expands. A material detector near the distal end of the catheter body may measure circumferential material distribution, and a power source selectively energizes the electrodes to eccentrically treat of a body lumen.

U.S. Pat. No. 9,757,180 to Gelfand, et al., describes systems, devices, and methods for treating a patient having a sympathetically mediated disease associated at least in part with augmented peripheral chemoreflex or heightened sympathetic activation. The treatments include ablating one or more peripheral chemoreceptors or associated afferent nerves to reduce or remove afferent neural signals from the peripheral chemoreceptor.

U.S. Pat. No. 9,474,486 to Eliason, et al., describes an electrophysiology catheter including an elongated, deformable shaft having a proximal end and a distal end and a basket electrode assembly coupled to the distal end of the shaft. The basket electrode assembly has a proximal end and a distal end and is configured to assume a compressed state and an expanded state. The electrode assembly further includes one or more tubular splines having a plurality of electrodes disposed thereon and a plurality of conductors. Each of the plurality of conductors extends through the tubular spline from a corresponding one of the plurality of electrodes to the proximal end of the basket electrode assembly. The tubular splines are configured to assume a non-planar (e.g., a twisted or helical) shape in the expanded state.

U.S. Pat. No. 9,060,756 to Bencini, et al., describes a method of ablating body tissue including: (a) locating an inflatable balloon portion of a cryotherapy balloon catheter at a treatment site internal to a patient's body, and inflating the inflatable balloon portion; (b) employing electrodes that are disposed on an expandable surface of the inflatable balloon portion to electrically characterize body tissue at the treatment site; (c) ablating the body tissue by supplying a cryotherapy agent to the inflatable balloon portion to cool the body tissue to a therapeutic temperature; (d) employing the electrodes to determine whether the ablating caused desired electrical changes in the body tissue; and (e) repeating (c) and (d) when it is determined that the ablating did not cause the desired electrical changes.

U.S. Pat. No. 10,362,952 to Basu, et al., describes a catheter for diagnosing and ablating tissue that has a stabilized spine electrode assembly. The stabilized spine electrode assembly has at least two spines secured to the catheter body at their proximal ends and at least one tether, secured between locations distal of the proximal ends of adjacent spines. The spines have a collapsed arrangement in which the spines are arranged generally along a longitudinal axis of the catheter body and an expanded arrangement in which at least a portion of each spine bows radially outwards from the longitudinal axis and the at least one tether exerts tension on the adjacent spines.

SUMMARY

There is provided in accordance with an embodiment of the present disclosure, a catheter apparatus configured to be inserted into a body part of a living subject, and including an elongated deflectable element including a distal end, an expandable basket assembly disposed at the distal end and including a plurality of splines and a plurality of electrodes disposed on the splines, an irrigation channel disposed in the elongated deflectable element, and an inflatable balloon disposed in the expandable basket assembly and including a plurality of irrigation holes in fluid connection with the irrigation channel.

Further in accordance with an embodiment of the present disclosure the splines are disposed circumferentially around the inflatable balloon.

Still further in accordance with an embodiment of the present disclosure the inflatable balloon is configured to fully inflate so that there is a gap of at least one millimeter between the fully inflated balloon and at least thirty percent of an inner surface area of the splines facing the inflatable balloon.

Additionally, in accordance with an embodiment of the present disclosure each of the splines includes an inner surface and an outer surface, the electrodes being disposed on the inner and outer surface of respective ones of the splines.

Moreover in accordance with an embodiment of the present disclosure the inflatable balloon and the expandable basket assembly include a distal end, the apparatus further including a support element connected to the distal end of the inflatable balloon and the distal end of the expandable basket assembly configured to maintain the gap of at least one millimeter between the fully inflated balloon and at least thirty percent of the inner surface area of the splines facing the inflatable balloon.

Further in accordance with an embodiment of the present disclosure respective ones of the splines include Nitinol.

Still further in accordance with an embodiment of the present disclosure the electrodes of the respective splines include Nitinol.

Additionally, in accordance with an embodiment of the present disclosure respective ones of the splines include respective polymer flex circuits.

Moreover, in accordance with an embodiment of the present disclosure at least ninety percent of the electrodes are disposed in a region of the expandable basket assembly, at least ninety percent of the irrigation holes of the inflatable balloon being disposed more proximally or more distally to the region.

Further in accordance with an embodiment of the present disclosure the electrodes are disposed in a region of the expandable basket assembly, the irrigation holes of the inflatable balloon being disposed more proximally or more distally to the region.

There is also provided in accordance with another embodiment of the present disclosure, a catheter apparatus configured to be inserted into a body part of a living subject, and including an elongated deflectable element including a distal end, an expandable basket assembly disposed at the distal end and including a plurality of splines and a plurality of electrodes disposed on the splines, and an inflatable balloon disposed in the expandable basket assembly and configured to fully inflate so that there is a gap of at least one millimeter between the fully inflated balloon and at least thirty percent of an inner surface area of the splines facing the inflatable balloon.

Still further in accordance with an embodiment of the present disclosure the splines are disposed circumferentially around the inflatable balloon.

Additionally, in accordance with an embodiment of the present disclosure each of the splines includes an inner surface and an outer surface, the electrodes being disposed on the inner and outer surface of respective ones of the splines.

Moreover in accordance with an embodiment of the present disclosure the inflatable balloon and the expandable basket assembly include a distal end, the apparatus further including a support element connected to the distal end of the inflatable balloon and the distal end of the expandable basket assembly configured to maintain the gap of at least one millimeter between the fully inflated balloon and at least thirty percent of the inner surface area of the splines facing the inflatable balloon.

Further in accordance with an embodiment of the present disclosure respective ones of the splines include Nitinol.

Still further in accordance with an embodiment of the present disclosure the electrodes of the respective splines include Nitinol.

Additionally, in accordance with an embodiment of the present disclosure respective ones of the splines include respective polymer flex circuits.

There is also provided in accordance with still another embodiment of the present disclosure, a medical system including a catheter configured to be inserted into a body part of a living subject, and including an elongated deflectable element including a distal end, an expandable basket assembly disposed at the distal end and including a plurality of splines and a plurality of electrodes disposed on the splines, and an inflatable balloon disposed in the expandable basket assembly, and an ablation power generator configured to be connected to the catheter, and apply an electrical signal to at least one of the electrodes to ablate a tissue of the body part.

Moreover, in accordance with an embodiment of the present disclosure the catheter includes an irrigation channel disposed in the elongated deflectable element, and wherein the inflatable balloon includes a plurality of irrigation holes in fluid connection with the irrigation channel.

Further in accordance with an embodiment of the present disclosure the inflatable balloon is configured to fully inflate so that there is a gap of at least one millimeter between the fully inflated balloon and at least thirty percent of an inner surface area of the splines facing the inflatable balloon.

Still further in accordance with an embodiment of the present disclosure each of the splines includes an inner surface and an outer surface, the electrodes being disposed on the inner and outer surface of respective ones of the splines.

Additionally, in accordance with an embodiment of the present disclosure at least ninety percent of the electrodes are disposed in a region of the expandable basket assembly, at least ninety percent of the irrigation holes of the inflatable balloon being disposed more proximally or more distally to the region.

Moreover, in accordance with an embodiment of the present disclosure the electrodes are disposed in a region of the expandable basket assembly, the irrigation holes of the inflatable balloon being disposed more proximally or more distally to the region.

Further in accordance with an embodiment of the present disclosure the ablation power generator is configured to apply the electrical signal between ones of the electrodes to perform irreversible electroporation of the tissue of the body part.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
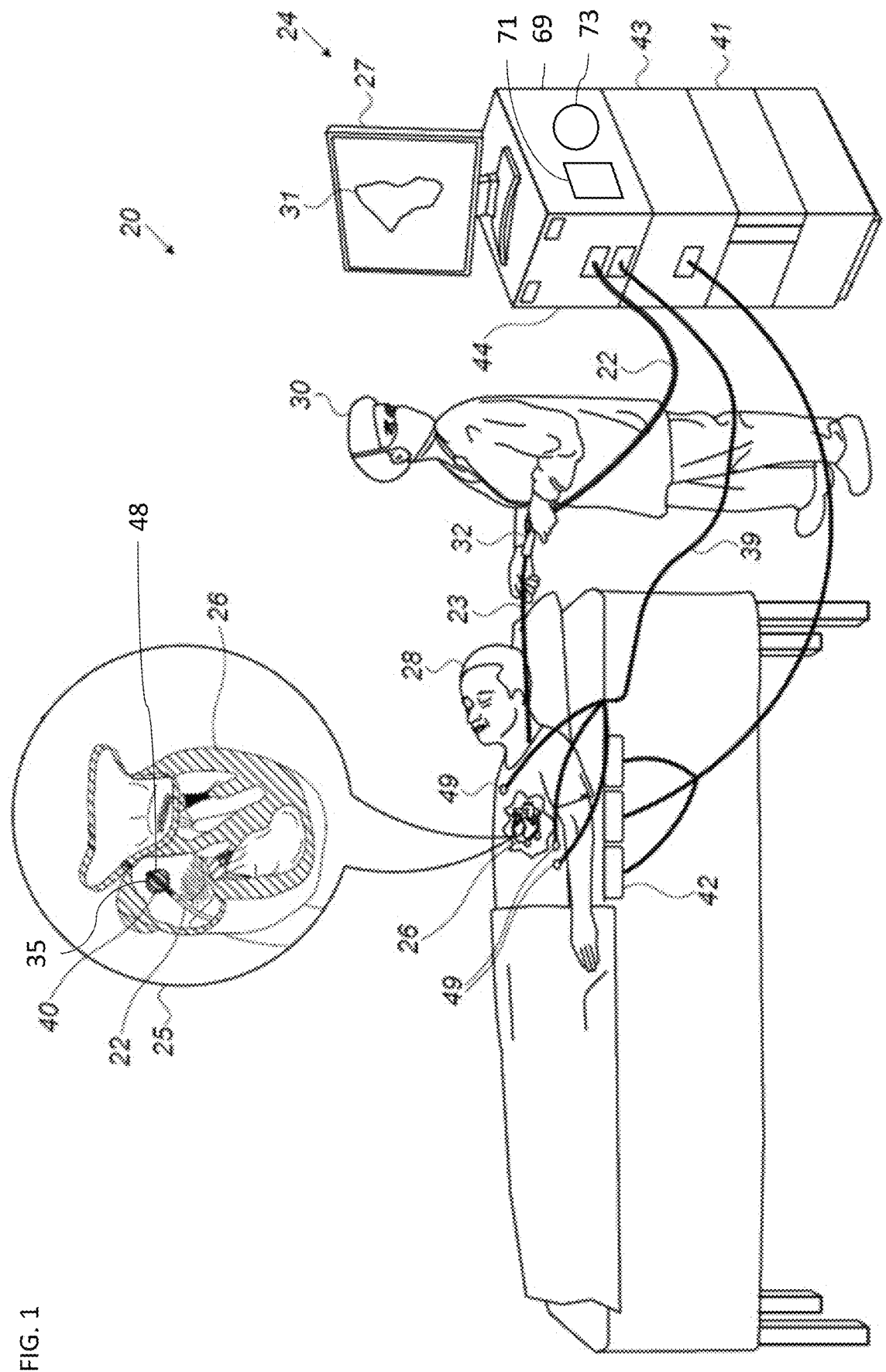
FIG. 1 is a schematic view of a medical system constructed and operative in accordance with an embodiment of the present invention.

Irrigation is commonly used with catheters to provide cooling during medical procedures such as radio-frequency (RF) ablation, for example. One solution for providing irrigation in a basket-type catheter is to have an irrigation channel run through the catheter which terminates in the middle of the basket. Irrigation fluid may then be pumped through the irrigation channel to the distal end of the irrigation channel where the irrigation fluid exits and provides cooling to tissue in the region of the basket as well as diluting blood locally. However, the irrigation is not very well directed and although it may be sufficient for electroporation, which does not generate much heat, it is generally not sufficient to reduce heat created during RF ablation. Another problem encountered with basket catheters is that the basket needs to be in a collapsed or semi-collapsed form during insertion into the body and then deployed to its expanded form in a body cavity. The requirement to be able to collapse and expand the basket adds further complications to providing effective irrigation as an irrigation channel may interfere with the expansion and collapsing of the basket. An additional problem encountered with basket catheters (whether used for ablation or diagnosis) is that during use, it has been found that blood clots may be created within the basket and stagnate there.

Embodiments of the present invention, solve the above problems by providing a catheter with an expandable basket assembly including electrodes thereon, with an inflatable balloon installed in the expandable basket assembly. When deployed, the balloon is inflated in the expanded basket assembly and acts to displace blood from the interior of the basket assembly to prevent blood clots being created within the basket assembly. Additionally, the balloon may include irrigation holes through which irrigation fluid is pumped to cool the electrodes in use. The balloon enables strategically placing the irrigation holes with respect to the electrodes to enhance cooling during use.

In some embodiments, the fully inflated balloon touches the interior surface of the expanded basket assembly. When there is no, or little, gap between the fully inflated balloon and the interior surface of the expanded basket assembly, blood is prevented from entering the interior of the basket assembly thereby preventing blood clots. In other embodiments, there is a gap between the fully inflated balloon and the interior surface of the expanded balloon. When there is a gap, the electrodes may be irrigated more efficiently (depending on the irrigation and electrode configuration), and the inner surface of the basket may include electrodes thereby increasing the electrode surface area that can be used for ablation.

In some embodiments, the catheter includes an elongated deflectable element, and an expandable basket assembly disposed at the distal end of the deflectable element. The basket assembly includes splines and electrodes placed on the splines. The catheter includes an inflatable balloon disposed in the expandable basket assembly with the splines being disposed circumferentially around the inflatable balloon.

In some embodiments, at least some of the splines include Nitinol. In some embodiments, the electrodes of the respective splines include Nitinol. For example, Nitinol splines are selectively covered with an insulating cover to leave electrodes exposed, or the Nitinol splines are covered and windows are opened in the covers to reveal electrodes. In other embodiments, the splines include respective polymer flex circuits. The flex circuits may be supported using Nitinol supports running along at least a given length of each spline.

In some embodiments, the catheter includes an irrigation channel disposed in the elongated deflectable element, and the inflatable balloon includes irrigation holes in fluid connection with the irrigation channel. In some embodiments, the electrodes are disposed in a region of the expandable basket assembly, and the irrigation holes of the inflatable balloon (when the balloon is fully inflated) are disposed more proximally or more distally to the electrode region (when the basket is fully expanded).

In some embodiments, the catheter includes an irrigation channel disposed in the elongated deflectable element, and the inflatable balloon includes irrigation holes in fluid connection with the irrigation channel. In some embodiments, at least ninety percent of the electrodes are disposed in a region of the expandable basket assembly, and at least ninety percent of the irrigation holes of the inflatable balloon (when the balloon is fully inflated) are disposed more proximally or more distally to the electrode region (when the basket is fully expanded).

In other embodiments, the inflatable balloon does not include irrigation holes. In those embodiments, irrigation may optionally be performed using other methods.

In some embodiments, the inflatable balloon is configured to fully inflate so that there is a gap of at least one millimeter between the fully inflated balloon and at least part (e.g., at least thirty percent) of an inner surface area of the splines (of the fully expanded basket assembly) facing the inflatable balloon. The balloon may optionally include irrigation holes. In some embodiments, a support element is connected to the distal end of the inflatable balloon and the distal end of the expandable basket assembly and maintains the gap between the fully inflated balloon and the splines of the fully expanded basket assembly. In some embodiments, when a gap is maintained, electrodes may be disposed on the inner and outer surface of each spline thereby increasing the electrode surface area for use in ablation. The electrode on the inner surface may be integral with, or connected to an electrode on the outer surface. In some embodiments, the fully inflated balloon touches the splines.

The system may include an ablation power generator connected to the catheter, and applies an electrical signal to the electrode(s) to ablate tissue of the body part. In some embodiments, the ablation power generator applies an electrical signal between the electrodes to perform irreversible electroporation of tissue of the body part.

System Description

Reference is now made to FIG. 1, which is a schematic view of a medical system 20 constructed and operative in accordance with an embodiment of the present invention. The system 20 includes a catheter 40 configured to be inserted into a body part of a living subject (e.g., a patient 28). A physician 30 navigates the catheter 40 (for example, a basket catheter produced Biosense Webster, Inc. of Irvine, Calif., USA), to a target location in a heart 26 of the patient 28, by manipulating an elongated deflectable element 22 of the catheter 40, using a manipulator 32 near a proximal end of the catheter 40, and/or deflection from a sheath 23. In the pictured embodiment, physician 30 uses catheter 40 to perform electro-anatomical mapping of a cardiac chamber and ablation of cardiac tissue.

Catheter 40 includes an expandable basket assembly 35, which is inserted in a folded configuration, through sheath 23, and only after the catheter 40 exits sheath 23 does the basket assembly 35 regain its intended functional shape. By containing basket assembly 35 in a folded configuration, sheath 23 also serves to minimize vascular trauma on its way to the target location.

Catheter 40 includes a plurality of electrodes 48 for sensing electrical activity and/or applying ablation power to ablate tissue of the body part. Catheter 40 may incorporate a magnetic sensor (not shown in FIG. 1) at the distal edge of deflectable element 22 (i.e., at the proximal edge of the basket assembly 35). Typically, although not necessarily, the magnetic sensor may be a Triple-Axis Sensor (TAS) or a Dual-Axis Sensor (DAS), or a SAS by way of example only, based for example on sizing considerations. A second magnetic sensor (not shown) may be included at any suitable position on the assembly 35. The second magnetic sensor may be a TAS, a DAS, or a SAS by way of example only, based for example on sizing considerations. The magnetic sensors and electrodes 48 disposed on the assembly 35 are connected by wires running through deflectable element 22 to various driver circuitries in a console 24.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between the magnetic sensors. Patient 28 is placed in a magnetic field generated by a pad containing one or more magnetic field generator coils 42, which are driven by a unit 43. The magnetic fields generated by coil(s) 42 transmit alternating magnetic fields into a region where the body-part is located. The transmitted alternating magnetic fields generate signals in the magnetic sensors, which are indicative of position and/or direction. The generated signals are transmitted to console 24 and become corresponding electrical inputs to processing circuitry 41.

The method of position and/or direction sensing using external magnetic fields and magnetic sensors, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

Processing circuitry 41, typically part of a general-purpose computer, is further connected via a suitable front end and interface circuits 44, to receive signals from body surface-electrodes 49. Processing circuitry 41 is connected to body surface-electrodes 49 by wires running through a cable 39 to the chest of patient 28.

In an embodiment, processing circuitry 41 renders to a display 27, a representation 31 of at least a part of the catheter 40 and a mapped body-part, responsively to computed position coordinates of the catheter 40.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The medical system 20 may also include an ablation power generator 69 (such as an RF signal generator) configured to be connected to the catheter 40, and apply an electrical signal to the electrodes 48. The medical system 20 may also include an irrigation reservoir 71 configured to store irrigation fluid, and a pump 73 configured to be connected to the irrigation reservoir 71 and the catheter 40, and to pump the irrigation fluid from the irrigation reservoir 71 through an irrigation tube of the catheter 40 as described in more detail with reference to FIGS. 2, 3, and 5.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

Figure 2:
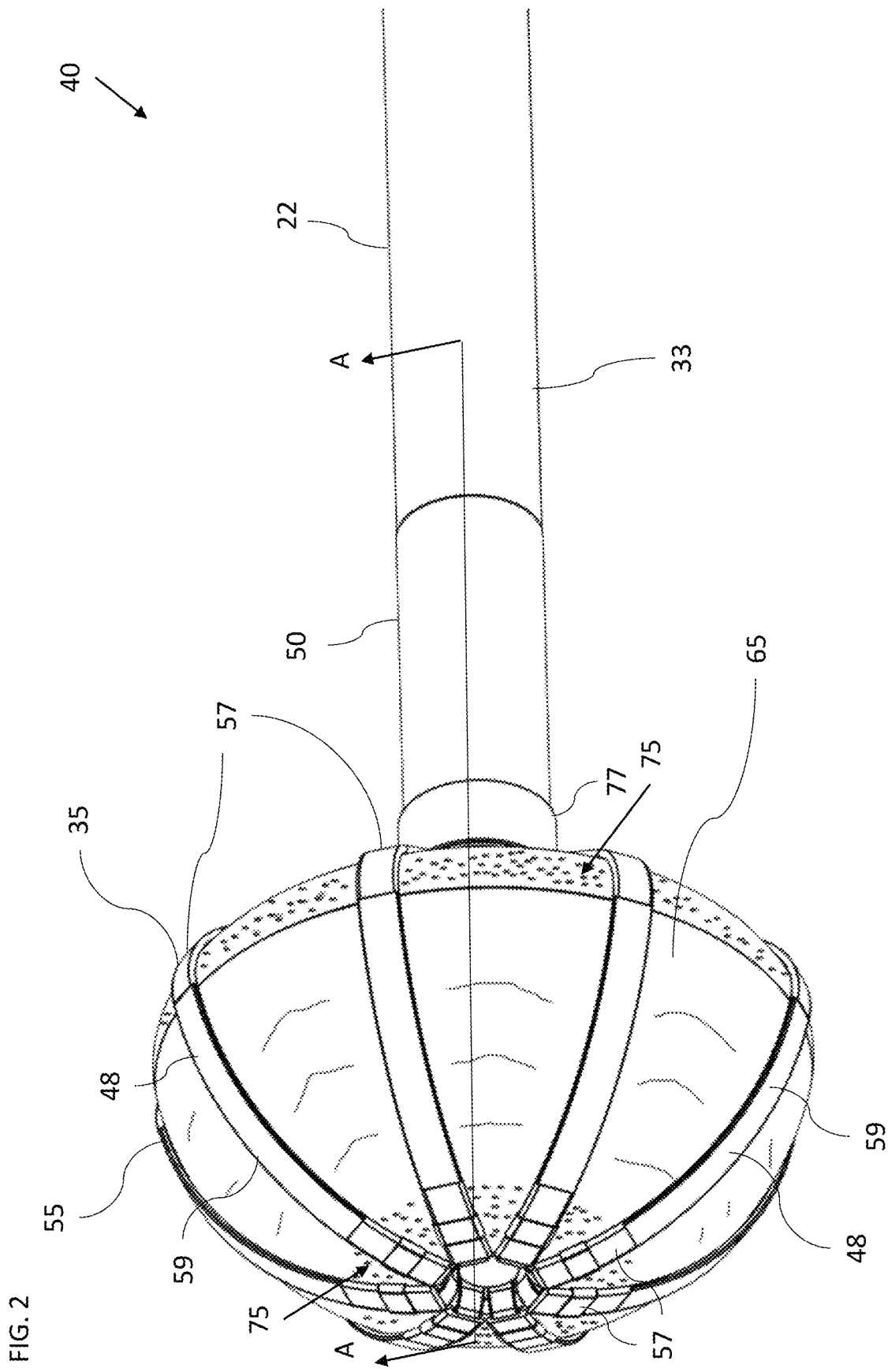
FIG. 2 is a schematic view of a catheter constructed and operative in accordance with an embodiment of the present invention.

Reference is now made to FIG. 2, which is a schematic view of the catheter 40 constructed and operative in accordance with an embodiment of the present invention.

The catheter 40 is configured to be inserted into a body part (e.g., the heart 26 (FIG. 1)) of a living subject. The deflectable element 22 of the catheter 40 has a distal end 33. The deflectable element 22 may be produced from any suitable material, for example, polyurethane or polyether block amide. The assembly 35 is disposed distally to the deflectable element 22 and may be connected to the deflectable element 22 via a proximal coupling member 50 at the distal end 33. The proximal coupling member 50 typically comprises a hollow tube and may be formed from any suitable material, for example, but not limited to polycarbonate with or without glass filler, polyether ether ketone (PEEK) with or without glass filler, polyimide, polyamide, or Polyetherimide (PEI) with or without glass filler. The coupling member 50 may formed as an integral part of the deflectable element 22 or as part of the basket assembly 35 or as a separate element which connects with the deflectable element 22 and the basket assembly 35. As used herein, the term "distal" means that a referenced component is further away from the operator and "proximal" means that the referenced component is closer to the operator of the catheter.

The assembly 35 may include multiple splines 55 (only one labeled for the sake of simplicity), such as flexible strips with the electrodes 48 (only some labeled for the sake of simplicity) being disposed on the splines 55. In the embodiment of FIG. 2, each spline 55 includes a single electrode 48. The assembly 35 may include any suitable number of electrodes 48 with multiple electrodes 48 per spline 55.

In some embodiments, at least some of the splines 55 include Nitinol. In some embodiments, the electrodes 48 of respective ones of the splines 55 include Nitinol. In other embodiments, respective ones of the splines 55 include respective polymer flex circuits. The flex circuits may be supported using Nitinol supports running along at least a length of each spline 55.

In the embodiment of FIG. 2, each spline 55 is formed from Nitinol which is selectively covered with insulating material in the distal and proximal regions 57 (only some labeled for the sake of simplicity) of the splines 55 leaving a central region 59 (only some labeled for the sake of simplicity) of the splines 55 as an electrically active region to perform mapping and/or perform ablation or electroporation, by way of example. The structure of the assembly 35 may vary. For example, splines 55 (or other splines) may include flexible printed circuit boards (PCBs), or any suitable shape-memory alloy.

In some embodiments, the relaxed state of the basket assembly 35 is the expanded deployed form. The basket assembly 35 is configured to collapse into the collapsed form when the catheter 40 is retracted in a sheath 23 (FIG. 1) and is configured to expand to the expanded deployed form when the catheter 40 is removed from the sheath 23. The relaxed shape of the basket assembly 35 may be set by forming the splines 55 from any suitable resilient material such as Nitinol or PEI. In other embodiments, the relaxed state of the expandable basket assembly 35 is the collapsed form and the expandable basket assembly 35 is expanded by retracting a pulling element (e.g., puller wire) disposed in the length of the elongated deflectable element 22 and connected to the distal end of the expandable basket assembly 35.

The catheter 40 includes an inflatable balloon 65 disposed in the expandable basket assembly 35. The splines 55 are generally disposed circumferentially around the inflatable balloon 65. In the embodiment shown in FIG. 2, the inflatable balloon 65 fully inflates so that it touches the splines 55 (along 90% or more of the length of each spline 55) of the fully expanded expandable basket assembly 35. In other embodiments, described in more detail with reference to FIG. 6, there is a gap of at least 1 mm between the fully inflated balloon 65 and at least 30% of the inner surface area of the splines 55 of the fully expanded expandable basket assembly 35.

Figure 3A:
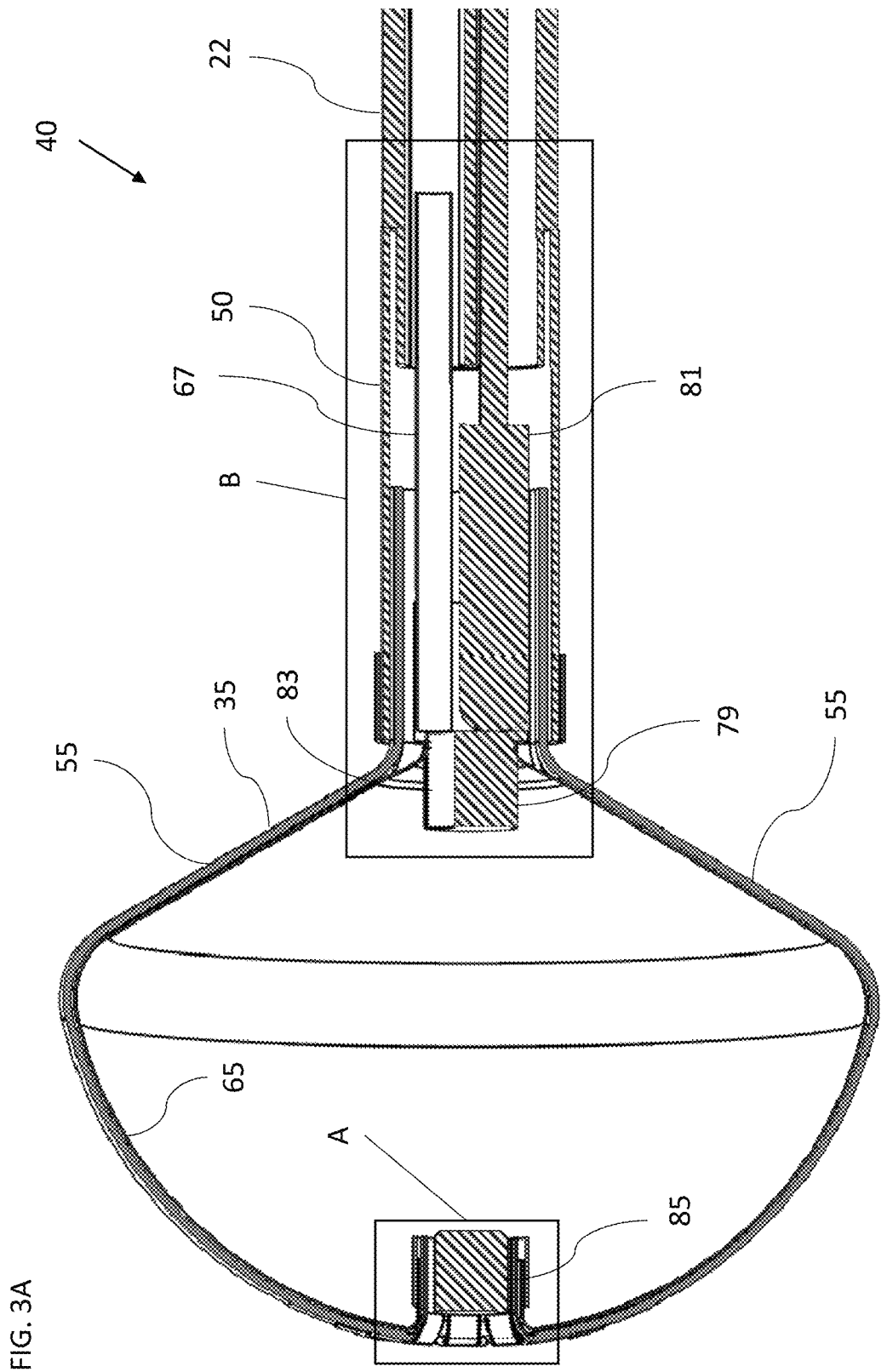
FIG. 3A is a cross-sectional view of the catheter of FIG. 2 along line A:A.

In some embodiments, the catheter 40 includes an irrigation channel 67 (shown in FIGS. 3A and 5) disposed in the elongated deflectable element 22. In the embodiment shown in FIG. 2, the inflatable balloon 65 is shown including a plurality of irrigation holes 75. The irrigation holes 75 are in fluid connection with the irrigation channel 67 (FIG. 3A).

In some embodiments, the irrigation holes 75 are disposed in one or more regions of the inflatable balloon 65. In other embodiments, the irrigation holes 75 are disposed over the inflatable balloon 65. In some embodiments, the irrigation holes 75 are mainly disposed in regions of the inflatable balloon 65 which are not close to the electrodes 48. In some embodiments, the electrodes 48 are disposed in a given region of the expandable basket assembly 35, and the irrigation holes 75 of the inflatable balloon 65 are disposed more proximally or more distally (with respect to a plane perpendicular to the axis of the non-deflected catheter 40) to the given region when the inflatable balloon 65 and the expandable basket assembly 35 are fully expanded. In some embodiments, at least ninety percent of the electrodes 48 are disposed in a given region of the expandable basket assembly 35, and at least ninety percent of the irrigation holes 75 of the inflatable balloon 65 are disposed more proximally or more distally (with respect to a plane perpendicular to the axis of the non-deflected catheter 40) to the given region when the inflatable balloon 65 and the expandable basket assembly 35 are fully expanded.

In other embodiments, the inflatable balloon 65 does not include irrigation holes. In these embodiments, irrigation may optionally be performed using any suitable method.

The ablation power generator 69 (FIG. 1) is configured to be connected to the catheter 40, and apply an electrical signal to at least one of the electrodes 48 (e.g., between two or more of the electrodes 48 or between one or more of the electrodes 48 and a proximal electrode 77 disposed at the distal end of the elongated deflectable element 22 or with a reference electrode) to ablate tissue of the body part (e.g., heart 26). In some embodiments, the ablation power generator 69 is configured to apply the electrical signal between one or more of the electrodes 48 to perform irreversible electroporation of the tissue of the body part. The inflatable balloon 65 helps prevent the electrical signal from mainly conducting through the center of the expandable basket assembly 35 and instead enhances conduction of the electrical signal through the tissue of the body part.

The inflatable balloon 65 may include a biocompatible material, such as polyurethane, polyether block amide, silicone, nylon, or polyester. Typically, the balloon would have a wall thickness between 0.0005" and 0.005". The irrigation holes 75 may have any suitable diameter, for example, in the range of about 0.01 mm to 0.125 mm, e.g. 0.075 mm. The inflatable balloon 65 may include any suitable number of discrete holes 75, for example, between 1 and 200, e.g. 50. In some embodiments, irrigation holes 75 may include laser or mechanically drilled holes.

The pump 73 (FIG. 1) is configured to pump irrigation fluid from the irrigation reservoir 71 (FIG. 1) via the irrigation channel 67 (FIG. 3A) into the inflatable balloon 65 and through the irrigation holes 75. The irrigation fluid is used to inflate the inflatable balloon 65. In embodiments, where the inflatable balloon 65 does not include irrigation holes, the inflatable balloon 65 may be inflated with any suitable fluid, such as saline or a gas.

Reference is now made to FIG. 3A, which is a cross-sectional view of the catheter 40 of FIG. 2 along line A:A. FIG. 3A (inside block A) shows the distal ends of the inflatable balloon 65 and the splines 55 (only two labeled for the sake of simplicity) folded over and connected to a distal connector 85, which in some embodiments is a tube (e.g., polymer tube) or slug (e.g., polymer slug). The distal connector 85 is described in more detail with reference to FIG. 4.

In some embodiments, the splines 55 and/or the inflatable balloon 65 may be connected to the distal connector 85 without being folded over so that when the basket assembly 35 is collapsed the splines 55 are approaching a flat formation along their length.

FIG. 3A (inside block B) shows that the proximal ends of the splines 55 are connected to the inner surface of the proximal coupling member 50. The proximal end of the inflatable balloon 65 is connected to a proximal connector 79 (for example, a polymer slug), which is secured to the proximal coupling member 50. The proximal connector 79 is described in more detail with reference to FIG. 5. FIG. 3A also shows the irrigation channel 67 (which extends through the deflectable element 22, the proximal coupling member 50, and a slot 83 in the proximal connector 79), and a position sensor 81 (e.g., a magnetic position sensor).

Figure 3B:
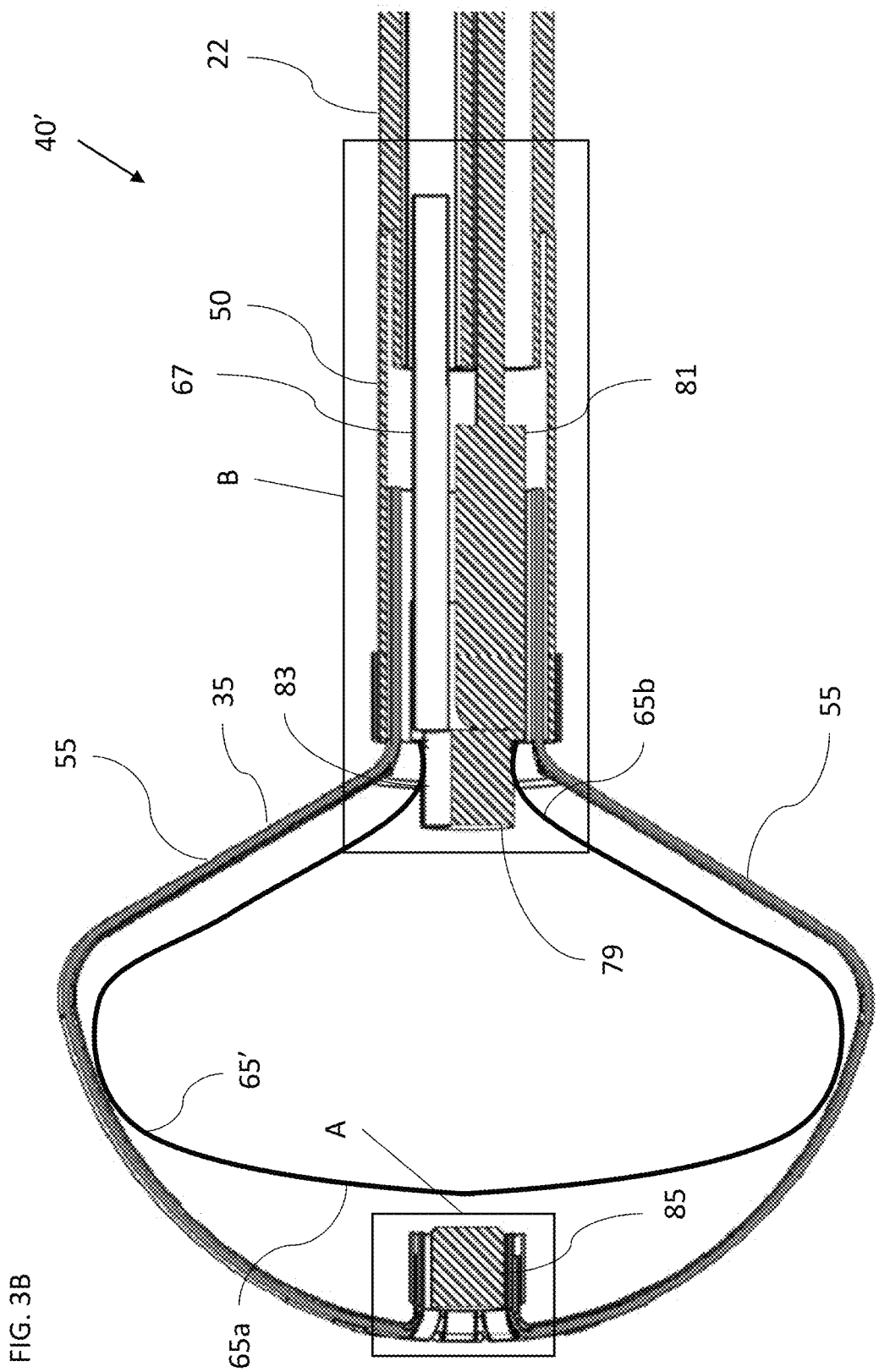
FIG. 3B is a cross-sectional view of an alternate embodiment of the device shown in FIG. 2 with a balloon uncoupled to distal end of the basket member.

In FIG. 3B, an alternate catheter end effector 40' is shown which has a balloon 65' arranged so that a distal balloon portion 65 a is not fixed or coupled to the catheter distal connector 85. That is, balloon 65' has a free distal balloon portion 65 a (i.e., unconnected to distal connector 85) with the proximal balloon portion 65 b coupled to the proximal coupling member 50 so that the balloon 65' is free to conform to the internal boundary of catheter splines 55. Balloon 65' in FIG. 3B is different in those aspects as compared to balloon 65 in FIG. 3A.

Figure 4:
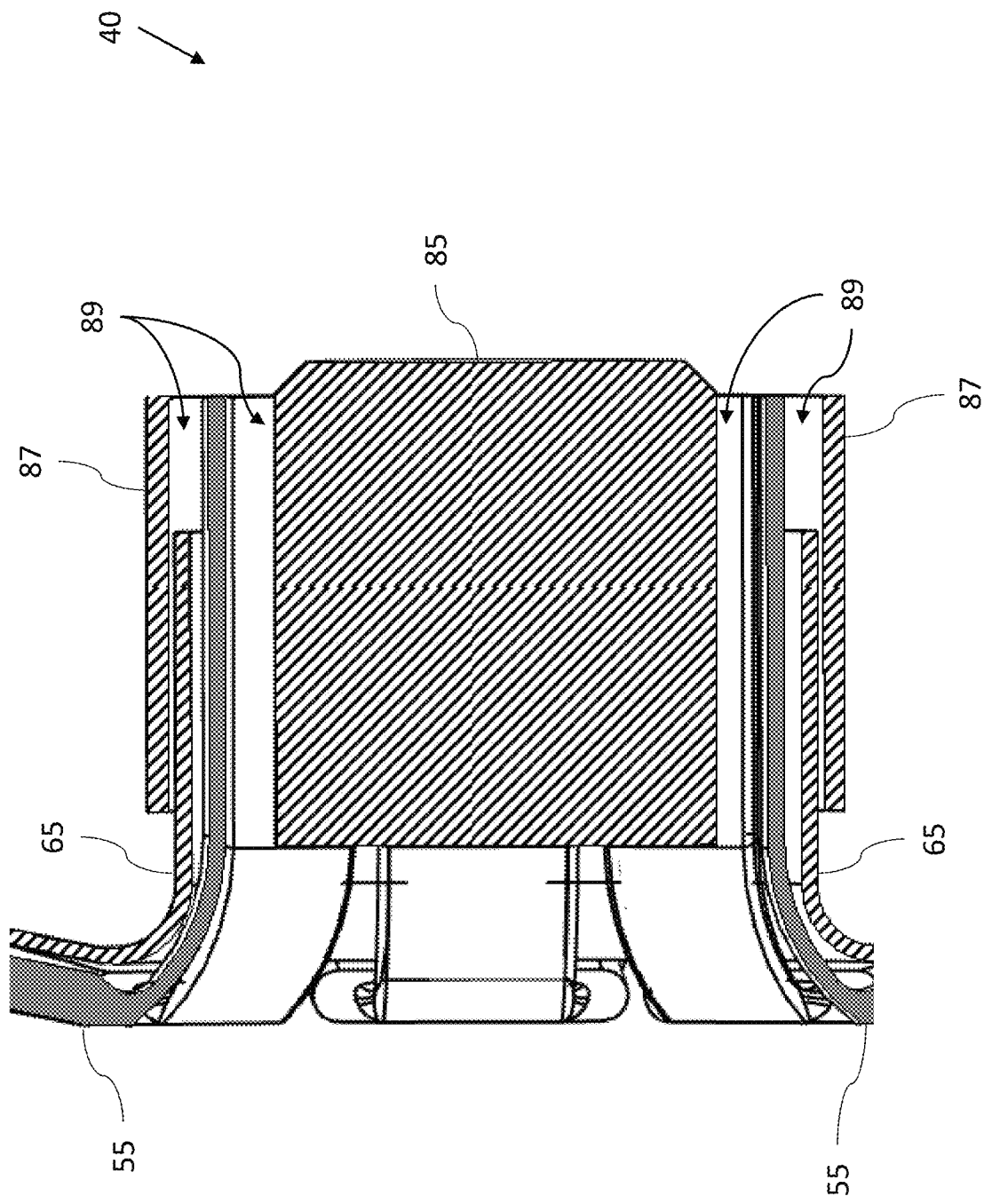
FIG. 4 is a more detailed cross-sectional view of the catheter inside block A of FIG. 3A.

Reference is now made to FIG. 4, which is a more detailed cross-sectional view of the catheter 40 inside block A of FIG. 3A. The splines 55 are secured to the distal connector 85. The distal end of the inflatable balloon 65 is secured between the splines 55 and a distal securing ring 87. An adhesive or epoxy layer 89 is disposed between the distal securing ring 87 and the distal connector 85 securing the splines 55 and the inflatable balloon 65 in place. In some embodiments, the inflatable balloon 65 and the splines 55 may be secured between the distal connector 85 and distal securing ring 87 using a pressure fit and/or any suitable adhesive. The distal connector 85 and the distal securing ring 87 may be formed from any suitable material, for example, but not limited to polycarbonate with or without glass filler, PEEK with or without glass filler, or PEI with or without glass filler. The distal connector 85 also functions as a slug to plug the distal end of the inflatable balloon 65.

Figure 5:
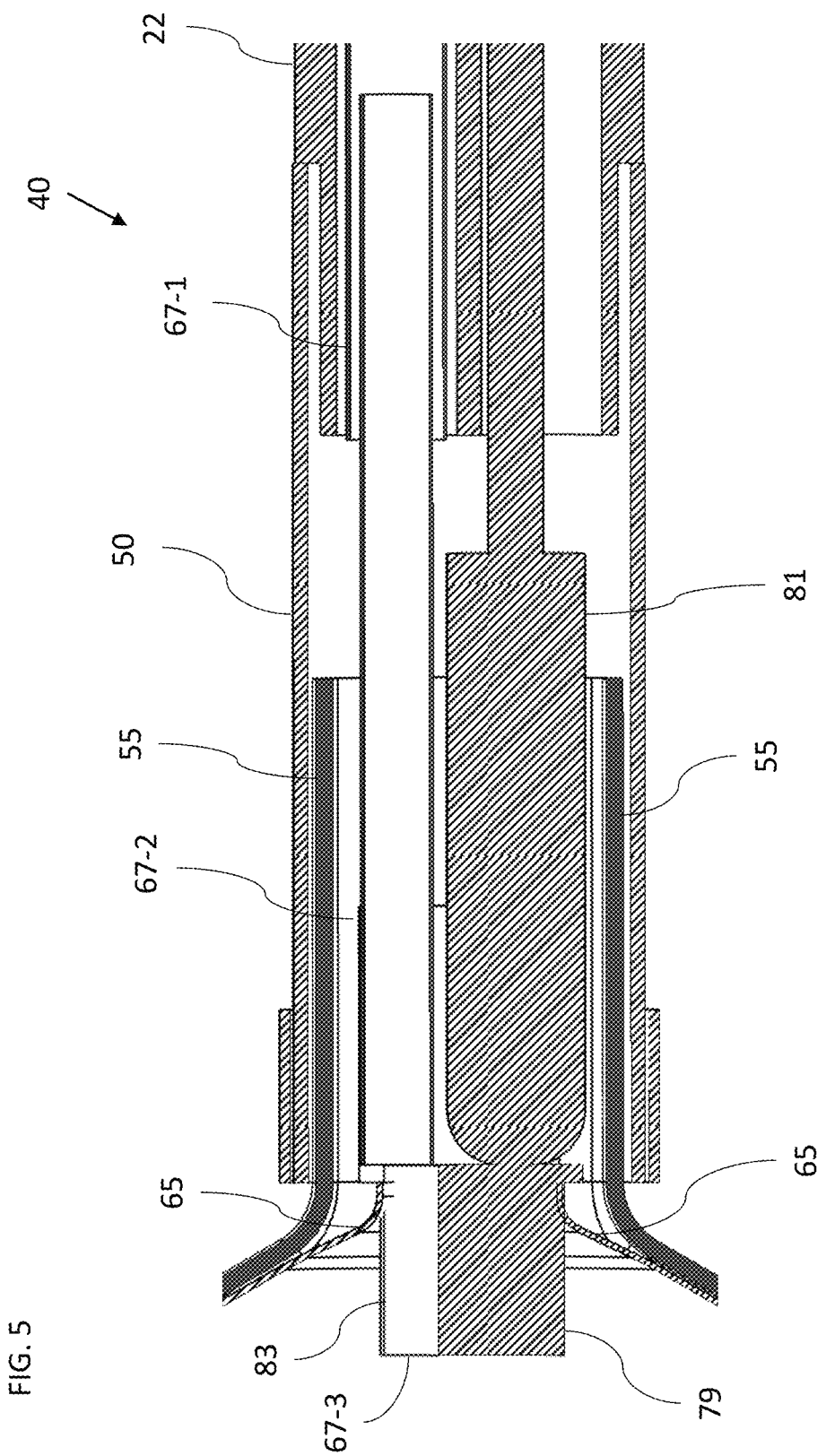
FIG. 5 is a more detailed cross-sectional view of the catheter inside block B of FIG. 3A.

Reference is now made to FIG. 5, which is a more detailed cross-sectional view of the catheter 40 inside block B of FIG. 3A or FIG. 3B.

FIG. 5 shows the proximal connector 79 and the slot 83. The slot 83 allows the irrigation channel 67-3 and electrical wires (e.g., for connection to one or more electrodes and/or sensors) to traverse the proximal connector 79. The irrigation channel 67-2 connects to the irrigation channel 67-3, which is narrower so that it fits in the slot 83. The inflatable balloon 65 is connected to the proximal connector 79, for example using adhesive. The inflatable balloon 65 may be connected to the proximal connector 79 using any suitable connection method.

The proximal ends of the splines 55 are secured between the proximal coupling member 50 and the position sensor 81 and the irrigation channel 67-2. The splines 55 may be secured to the proximal coupling member 50 using a pressure fit and/or any suitable adhesive. The irrigation channel 67-2 is connected to the irrigation channel 67-1, which is disposed in the elongated deflectable element 22.

The proximal connector 79 may be formed from any suitable material, for example, but not limited to polycarbonate with or without glass filler, PEEK with or without glass filler, or PEI with or without glass filler.

Figure 6:
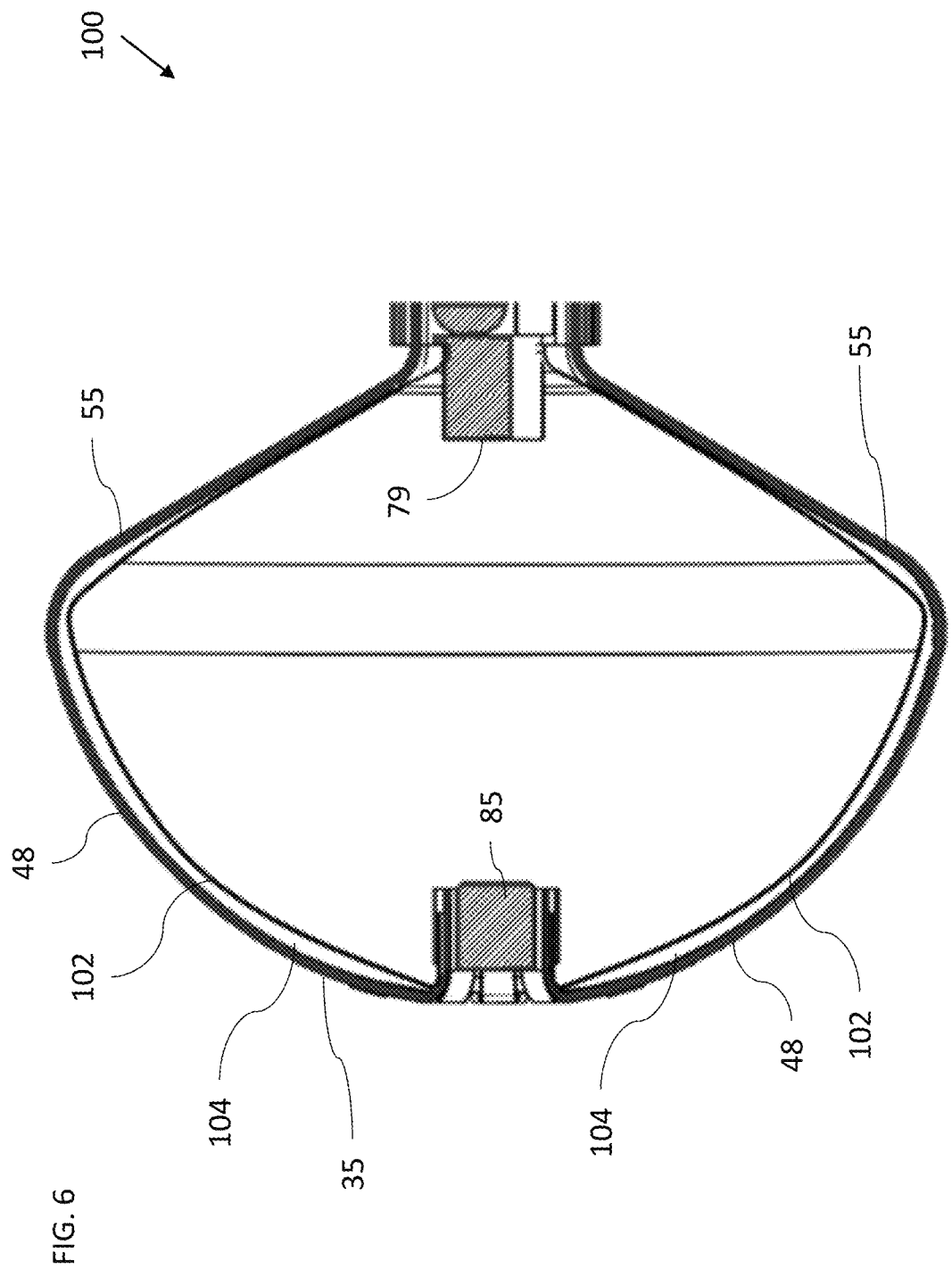
FIG. 6 is a cross-sectional view of a catheter constructed and operative in accordance with an alternative embodiment of the present invention.

Reference is now made to FIG. 6, which is a cross-sectional view of a catheter 100 constructed and operative in accordance with an alternative embodiment of the present invention. The catheter 100 is substantially the same as the catheter 40 of FIGS. 1-5 except for the following differences.

The catheter 100 includes an inflatable balloon 102, which is configured to fully inflate so that there is a gap 104 of at least one millimeter between the fully inflated balloon 102 and at least part (e.g., at least thirty percent) of an inner surface area of the splines 55 facing the inflatable balloon 102. The "inner surface" is defined as the surface of the splines 55 facing the inflatable balloon 102.

In some embodiments, the inflatable balloon 102 includes irrigation holes (not shown). In other embodiments, the inflatable balloon 102 does not include irrigation holes.

In some embodiments, the catheter 100 includes a support element such as the distal connector 85 connected to the distal end of the inflatable balloon 102 and the distal end of the expandable basket assembly 35 (and/or the proximal connector 79 connected to the proximal end of the inflatable balloon 102 and the proximal end of the expandable basket assembly 35) configured to maintain the gap 104 of at least one millimeter between the fully inflated balloon 102 and at least part (e.g., at least thirty percent) of the inner surface area of the splines 55 facing the inflatable balloon 102.

In some embodiments, the electrodes 48 are disposed on the inner and outer surface of respective ones of the splines 55. Using the inner and outer surfaces for the electrodes 48 provides a greater surface area for ablation. One of the electrodes 48 disposed on the inner surface of one of the splines 55 may be electrically connected to the corresponding electrode 48 on the outer surface of that spline 55. In some embodiments, a single electrode may extend from the inner surface to the outer surface (for example, when the spline 55 is formed from a conductor such as Nitinol).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed:

1. A catheter apparatus comprising: (a) an elongated deflectable element including a distal end; (b) an expandable basket assembly disposed at the distal end and comprising a plurality of splines and a plurality of electrodes disposed on the splines; (c) an irrigation channel disposed in the elongated deflectable element; (d) an inflatable balloon disposed in the expandable basket assembly and comprising a plurality of irrigation holes in fluid connection with the irrigation channel, each irrigation hole of the plurality of irrigation holes being angularly offset from each spline of the plurality of splines, at least ninety percent of the electrodes being disposed in a region of the expandable basket assembly, at least ninety percent of the irrigation holes of the inflatable balloon being disposed more proximally or more distally to the region.

2. The apparatus according to claim 1, the splines being disposed circumferentially around the inflatable balloon.

3. The apparatus according to claim 1, the inflatable balloon being configured to fully inflate so that there is a gap of at least one millimeter between the fully inflated balloon and at least thirty percent of an inner surface area of the splines facing the inflatable balloon.

4. The apparatus according to claim 3, each of the splines including an inner surface and an outer surface, the electrodes being disposed on the inner and outer surface of respective ones of the splines.

5. The apparatus according to claim 3, wherein the inflatable balloon and the expandable basket assembly include a distal end, the apparatus further comprising a support element connected to the distal end of the inflatable balloon and the distal end of the expandable basket assembly configured to maintain the gap of at least one millimeter between the fully inflated balloon and at least thirty percent of the inner surface area of the splines facing the inflatable balloon.

6. The apparatus according to claim 1, respective ones of the splines including Nitinol.

7. The apparatus according to claim 6, the electrodes of the respective splines including Nitinol.

8. The apparatus according to claim 1, respective ones of the splines including respective polymer flex circuits.

9. The apparatus according to claim 1, each of the splines including an inner surface and an outer surface, the electrodes being disposed on the inner and outer surface of respective ones of the splines.

10. The apparatus according to claim 1, the inflatable balloon and the expandable basket assembly including a distal end, the apparatus further comprising a support element connected to the distal end of the inflatable balloon and the distal end of the expandable basket assembly configured to maintain the gap of at least one millimeter between the fully inflated balloon and at least thirty percent of the inner surface area of the splines facing the inflatable balloon.

11. A medical system comprising: (a) a catheter including: (i) an elongated deflectable element including a distal end; (ii) an expandable basket assembly disposed at the distal end and comprising a plurality of splines and a plurality of electrodes disposed on the splines; and (iii) an inflatable balloon disposed in the expandable basket assembly, a distal portion of the expandable basket assembly being configured to seal a distal end of the inflatable balloon, the inflatable balloon being configured to fully inflate so that there is a gap of at least one millimeter between the fully inflated balloon and at least thirty percent of an inner surface area of the splines facing the inflatable balloon; and (b) an ablation power generator configured to be connected to the catheter, and apply an electrical signal to at least one of the electrodes to ablate a tissue; at least ninety percent of the electrodes being disposed in a region of the expandable basket assembly, the inflatable balloon comprising a plurality of irrigation holes and at least ninety percent of the irrigation holes of the inflatable balloon being disposed more proximally or more distally to the region.

12. The system according to claim 11, the catheter including an irrigation channel disposed in the elongated deflectable element, and the plurality of irrigation holes in fluid connection with the irrigation channel.

13. The system according to claim 11, each of the splines including an inner surface and an outer surface, the electrodes being disposed on the inner and outer surface of respective ones of the splines.

14. The system according to claim 11, the ablation power generator being configured to apply the electrical signal between ones of the electrodes to perform irreversible electroporation of the tissue.

* * * * *